United States Patent [19]

Schaefer

[11] Patent Number: 4,576,976
[45] Date of Patent: Mar. 18, 1986

[54] PROCESS FOR THE PHOTOPOLYMERIZATION OF VINYL COMPOUNDS AND PHOTOPOLYMERIZABLE MATERIALS

[75] Inventor: Roland Schaefer, Friedrichsdorf, Fed. Rep. of Germany

[73] Assignee: Kulzer & Co., GmbH, Wehrheim, Fed. Rep. of Germany

[21] Appl. No.: 587,176

[22] Filed: Mar. 7, 1984

Related U.S. Application Data

[63] Continuation-in-part of Ser. No. 413,804, Sep. 1, 1982, Pat. No. 4,534,839.

[30] Foreign Application Priority Data

Sep. 15, 1981 [DE] Fed. Rep. of Germany ....... 3136484

[51] Int. Cl.$^4$ ................................................. C08F 2/50
[52] U.S. Cl. ........................................ 522/16; 522/26; 522/83; 522/92; 522/95; 522/63
[58] Field of Search ................................... 204/159.23

[56] References Cited

U.S. PATENT DOCUMENTS 3,440,052  4/1969  Heseltine ............................. 430/578
3,932,182  1/1976  Futaki et al. ..................... 260/562 R
4,071,424  1/1978  Dart et al. ....................... 204/159.19
4,131,729  12/1978  Schmitt et al. ................. 204/159.23
4,273,860  6/1981  Adin .................................... 430/338
4,282,309  8/1981  Laridon et al. ................. 204/159.15
4,284,706  8/1981  Clecak et al. ....................... 430/193

FOREIGN PATENT DOCUMENTS 2403211  1/1974  Fed. Rep. of Germany .
3136484  4/1983  Fed. Rep. of Germany .
124594  10/1978  Japan .

OTHER PUBLICATIONS

Brederick et al., "About CH-Active Polymerization Initiators" Macromolecular Chemie 92, 70–90, 1966.
Roffey, "Photopolymerization . . . " Wiley & Sons, 1982, pp. 70–72, 85–88.

Primary Examiner—John C. Bleutge
Assistant Examiner—A. H. Koeckert
Attorney, Agent, or Firm—Frishauf, Holtz, Goodman & Woodward

[57] ABSTRACT

Disclosed is a process for the photopolymerization of vinyl compounds and of photopolymerizable materials containing vinyl compounds and products produced thereby which are especially useful for dental materials. The process utilizes at least one photosensitizer of the formula

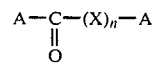

wherein X is selected from the group consisting of CO, $C(R^1)(R^2)$ and $C(R^3)(OR^4)$; wherein $R^1$, $R^2$, $R^3$, $R^4$ are each selected from the group consisting of hydrogen and a hydrocarbon radical;

n is 0 or 1; and

A is selected from hydrocarbon radicals which may be substituted and which may be bonded together with the proviso that when n is 1 and X is $C(R^1)(R^2)$, and when n is 0, A is an aromatic radical; and at least one reducing agent of formula (I) or (II)

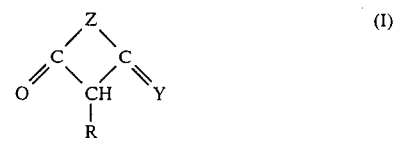

wherein

Y is selected from oxygen, sulfur or the group $NR^1$ where $R^1$ is a hydrogen atom or an alkyl group having 1–10 carbon atoms, preferably 1–5 carbon atoms;

Z is an alkylene group having 2 or 3 carbon atoms where one carbon atom can be substituted with one of the heteroatoms O and S or 2 carbon atoms with the heteroatoms O, S and/or N; and R is a substituted or unsubstituted alkyl group having 1–10 carbon atoms, preferably 1–5 carbon atoms or a substituted or unsubstituted aryl group, preferably a phenyl group,

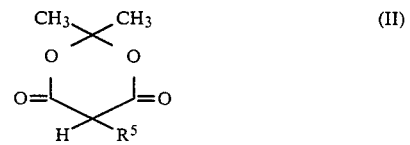

wherein $R^5$ is selected from the group consisting of alkyl, substituted alkyl, aryl, substituted aryl, aralkyl and substituted aralkyl.

19 Claims, No Drawings

PROCESS FOR THE PHOTOPOLYMERIZATION OF VINYL COMPOUNDS AND PHOTOPOLYMERIZABLE MATERIALS

This application is a continuation-in-part of Ser. No. 413,804, filed Sept. 1, 1982, now U.S. Pat. No. 4,534,839.

BACKGROUND OF THE INVENTION

The present invention provides a process for the photopolymerization of vinyl compounds in the presence of a photoinitiator.

Photopolymerization has many useful applications in the technical field, as for example, for the curing of lacquers and coatings, in the manufacture of printing plates and in letter press printing.

Photopolymerization is also useful in the dental field as well. Photopolymerizable materials are used in the preparation of dental fillings and sealings, of crowns, bridges artificial teeth and dentures (see, for example, British Pat. No. 569,974 and German Patent Publication Nos. 23 15 645, 23 57 324, 29 10 077 and 29 14 537).

British Pat. No. 1,408,265 (corresponding to U.S. Pat. No. 4,071,424) describes photopolymerizable materials which contain as a photoinitiator a mixture of:

(a) at least one photosensitizer of the formula

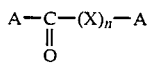

where X is CO, $C(R^1)(R^2)$ or $C(R^3)(OR^4)$, $R^1$, $R^2$, $R^3$, $R^4$, which may be the same or different, are hydrogen or hydrocarbyl groups, n is 0 or 1, and the groups A, which may be the same or different, are hydrocarbyl or substituted hydrocarbyl groups and in which the groups A may be further linked together by a direct link or by a divalent hydrocarbyl group, or in which the groups A together may form a fused aromatic ring system, the groups A being aromatic or substituted aromatic when n is 1 and X is $C(R^1)(R^2)$ and when n is 0, and (b) at least one reducing agent capable of reducing the photosensitizer when the photosensitizer is in an excited state and having the structure

where M is an element of Group VB of the Periodic Table and the units R, which may be the same or different, are hydrogen atoms, hydrocarbyl groups, substituted hydrocarbyl groups or groups in which two units R together with the element M form a cyclic ring system, no more than two of the units R being hydrogen atoms or substituted hydrocarbyl groups and, where element M is attached directly to an aromatic group R, at least one of the other units R has a

group attached to M.

British Pat. No. 1,465,897 discloses photopolymerizable materials useful in dentistry which contain as a photoinitiator a mixture of:

(a) at least one photosensitizer of the formula

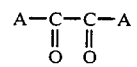

in which the groups A, which may be the same or different, are hydrocarbyl groups or sustituted hydrocarbyl groups; and (b) at least one reducing agent capable of reducing the photosennsitizer when the photosensitizer is in an excited state and having the formula

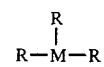

wherein M is an element or Group VB of the Periodic Table and the units R, which may be the same or different, are hydrogen atoms, hydrocarbyl groups, substituted hydrocarbyl groups, or groups in which two units R together with the element M form a cyclic ring system, no more than two of the units R being hydrogen atoms and the element M not being attached directly to an aromatic group.

The resulting mixtures can be cured by exposure to visible light or through ultraviolet rays. Examples of the photosensitizers include benzil, p,p'-dimethoxy benzil, benzoin, and camphorquinone. Reducing agents include propylamine, dimethylaminoethyl methacrylate, N,N'-dimethylaniline and piperidine.

It is the object of the present invention to provide a photoinitiator having (a) at least one photosensitizer, and (b) at least one reducing agent for the photopolymerization of vinyl compounds which effects a rapid curing and results in good color fastness of the polymerized substance.

SUMMARY OF THE INVENTION

The present invention provides a process for the photopolymerization of vinyl compounds in the presence of a photoinitiator comprising:

(a) at least one photosensitizer of the type described in British Pat. No. 1,408,265, the photosensitizer comprising:

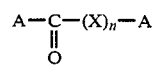

wherein X is selected from CO, $C(R^1)(R^2)$ or $C(R^3)(OR^4)$, wherein $R^1$, $R^2$, $R^3$ and $R^4$ are each selected from hydrogen or a hydrocarbon radical; n is 0 or 1; A are hydrocarbon radicals which may be substituted and which may be bonded together, with the proviso that when n is 1 and X is $C(R^1)(R^2)$, and when n is 0, then A is an aromatic radcial; and (b) as a reducing agent, at least one compound of formula (I) or (II)

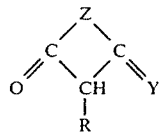

wherein

Y is selected from oxygen, sulfur or the group $NR^1$ where $R^1$ is a hydrogen atom or an alkyl group having 1–10 carbon atoms, preferably 1–5 carbon atoms;

Z is an alkylene group having 2 or 3 carbon atoms where one carbon atom can be substituted with one of the heteroatoms O and S or 2 carbon atoms with the heteroatoms O, S and/or N; and R is a substituted or unsubstituted alkyl group having 1–10 carbon atoms, preferably 1–5 carbon atoms or a substituted or unsubstituted aryl group, preferably a phenyl group.

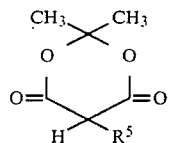

wherein $R^5$ is selected from the group consisting of alkyl (preferably having 1–5 carbon atoms), substituted alkyl wherein the alkyl radical preferably has 1–5 carbon atoms, aryl (preferably phenyl) substituted aryl, aralkyl (preferably benzyl) and substituted aralkyl. The preferred substituents for the substituted alkyl group are acyl, acyloxy, alkoxysulfonyl and aryloxysulfonyl. The preferred substituents for the substituted aryl group are alkyl, acyl, acyloxy, alkoxysulfonyl and aryloxysulfonyl. The preferred substituents for the substituted aralkyl group are alkyl, acyl, acyloxy, alkoxysulfonyl and aryloxysulfonyl.

The preferred reducing agents of formula (I) are selected from 5-alkyl and 5-aryl-barbituric acids, such as 5-butyl barbituric acid and 1-benzyl-5-phenyl barbituric acid. The preferred reducing agents of formula (II) are methylmeldrum acid, ethylmeldrum acid, benzylmeldrum acid and phenylmeldrum acid. The photoinitiators composed of camphorquinone and 5-alkyl or 5-arylbarbituric acids, and camphorquinone and methylmeldrum acid, ethylmeldrum acid, benzylmeldrum acid and phenylmeldrum acid have been proven to be especially advantageous.

The vinyl-polymers and copolymers obtained through the process according to the present invention do not display any discoloration.

The present process is applicable whenever monomer vinyl compounds, especially compositions containing these compounds, are to be photopolymerized by exposure to visible light and/or ultraviolet rays.

The vinyl compounds which may be polymerized in accordance with the present invention include all commonly used ethylenelike unsaturated compounds, especially vinyl chloride and esters of acrylic and methacrylic acids with monohydric and polyhydric alcohols. Also included are the so-called urethane acrylates and methacrylates and Bis-GMA, as shown in U.S. Pat. No. 3,066,112, which is the reaction product of Bis-phenol A and glycidylmethacrylate.

In practice, the photosensitizer is added to the vinyl compounds, especialy to the compositions containing these vinyl compounds in an amount of between $10^{-2}$ and 10% by weight, with respect to the vinyl compounds. The preferred amount is between $10^{-1}$ and 5% by weight. The reducing agent is also present in the same quantities.

The application of the process according to the invention has been especially beneficial in the field of dentistry, for the preparation of dental fillings and sealings, as well as crowns, bridges, artificial teeth and dentures.

In the following examples photopolymerizable compositions containing vinyl compounds and their polymerization according to the invention are described. The thickenss of the resulting solid body of the polymer is measured and serves as the means of comparing the activity of the photoinitiator.

EXAMPLES 1–3

A mixture of 7 g Bis-GMA 3 g triethyleneglycoldimethacrylate 30 g lithium aluminum silicate of fine particle size (85% by weight of the particles with a particle size <15 μm), and X photoinitiator (see Table 1)

is placed into a small glass tube (inside diameter 6 mm and 30 mm high) which is shielded with aluminum foil in such a way that no light can enter through the sides. The mixture is exposed to the radiation of a tungsten lamp (250 W/24 V made by Philips) at a distance of 17 cm for a period of 2 minutes.

The portion of the mixture which remained unpolymerized is removed and the thickness of the solid polymer was measured.

Table 1 reports the kind and quantity of the photoinitiator and the thickness of the layer.

TABLE 1

| EXAMPLE | INITIATOR | WEIGHT % | THICKNESS OF LAYER, mm |
|---|---|---|---|
| 1 | CAMPHOR QUINONE | .3 | 3.5 |
| 2 | CAMPHOR QUINONE + 5-BUTYLBARBITURIC ACID | .3 1.0 | >20 |
| 3 | CAMPHORQUINONE + 5-BUTYLBARBITURIC ACID | .3 .2 | 15 |

EXAMPLE 4 (Comparison)

A mixture corresponding to that of Example 2 is placed into a small glass tube (inside diameter 6 mm and 30 mm high) which is completely shielded with aluminum foil, so that upon exposure to radiation none of the radiation can effect polymerization. Thereafter, the small tube is exposed to the radiation of a tungsten lamp (250 W/24 V made by Philips) at a distance of 17 cm for two minutes. Polymerization of the mixture did not occur.

EXAMPLE 5 (Comparison)

A mixture corresponding to that of Example 2 is placed into a small glass tube (6 mm inside diameter and 30 mm high) and heated to 120° C. for 5 minutes. Polymerization of the mixture did not occur.

EXAMPLES 6–12

A mixture of
- 9.3 g Bis-GMA,
- 7.8 triethyleneglycoldimethyacrylate,
- 6.9 g urethanedimethacrylate, obtained by the reaction of 1 mol of trimethylhexamethylenediisocyanate with 2 moles of 2-hydroxyethylmethacrylate,
- 23.1 g silicon dioxide, of fine particle size, obtained by high temperature hydrolysis,
- 2.6 g aluminum oxide, of fine particle size,
- 50.3 g of splinter polymer obtained by the polymerization of a mixture of triethyleneglycoldimethacrylate and silicon dioxide of fine particle size, obtained by high temperature hydrolysis and powdering in a conventional manner (e.g. German Pat. No. 24 03 211), and X photoinitiator (see Table 2), is placed into a small glass tube (6 mm inside diameter and 30 mm high) which is shielded with aluminum foil in such a way that no light can enter through the sides. The mixture is exposed to the radiation of a tungsten lamp (250 W/24 V made by Philips) at a distance of 17 cm for 2 minutes. The portion of the mixture which did not polymerize is removed and the thickness of the layer of the formed body is measured.

Table 2 reports the kind and quantity of the photoinitiator and the thickness of the layer.

TABLE 2

| EXAMPLE | INITIATOR | WEIGHT % | THICKNESS OF LAYER, mm |
| --- | --- | --- | --- |
| 6 (COMPARISON) | CAMPHORQUINONE | .2 | 3 |
| 7 (COMPARISON) | CAMPHORQUINONE + N,N′DIMETHYL-p-TOLUIDINE | .2 .2 | 6.6 |
| 8 | CAMPHORQUINONE + METHYLMELDRUM ACID = METHYLMALONIC ACIDISO-PROPYLIDENE ESTER | .2 .2 | 5.2 |
| 9 | CAMPHORQUINONE + 1-BENZYL-5-PHENYL-BARBITURIC ACID | .2 1.0 | >20 |
| 10 | CAMPHORQUINONE 1-BENZYL-5-PHENYL-BARBITURIC ACID | .2 .2 | 19 |
| 11 | CAMPHORQUINONE + 5-BUTYLBARBITURIC ACID | .2 1. | >20 |
| 12 | CAMPHORQUINONE + 5-BUTYLBARBITURIC ACID | .2 .2 | 15 |

EXAMPLES 13–16

A mixture of
- 9.3 g Bis-GMA,
- 7.8 g triethyleneglycoldimethacrylate,
- 6.9 g urethanedimethacrylate, obtained by the reaction of 1 mol of trimethylhexamethylenediisocyanate with 2 moles of 2-hydroxyethylmethacrylate,
- 23.1 g silicon dioxide, in fine particle size, obtained by high temperature hydrolysis,
- 2.6 g aluminum oxide, in fine particle size,
- 50.3 g splinter polymer obtained by the polymerization of a mixture of triethyleneglycoldimethacrylate and silicon dioxide of fine particle size, obtained by high temperature hydrolysis and powdering in a conventional manner (e.g. German Pat. No. 24 03 211), and X photoinitiator (see Table 3) is placed into a tube (inside diameter 6 mm and 30 mm high) made of DELRIN, a polyacetal plastic, and exposed to radiation of a tungsten-halogen visible light fixture Translux made by kulzer for 20 seconds. The portion of the mixture which did not polymerize is removed and the thickness of the formed body of the polymer is measured.

The kind and quantity of the photoinitiator and the thickness of the layer are reported in Table 3.

TABLE 3

| EXAMPLE | INITIATOR | WEIGHT, % | THICKNESS OF LAYER, mm |
| --- | --- | --- | --- |
| 13 (COMPARISON) | CAMPHORQUINONE | .2 | 1.7 |
| 14 | CAMPHORQUINONE + 5-BUTYLBARBITURIC ACID | .2 1.0 | 3.0 |
| 15 (COMPARISON) | p,p′-DIMETHOXYBENZIL | .2 | .1 |
| 16 | p,p′-DIMETHOXYBENZIL + 5-BUTYLBARBITURIC ACID | .2 1.0 | 1.0 |

Test specimens with a diameter of 10 cm and a thickness of 2 mm made of photopolymerizable materials according to the invention, as described in the examples, are tested for color fastness in accordance with the standard for dental filling materials ISO 4049. The radiation apparatus used in this test (Suntest) is made by W. C. Hereaus GmbH.

After exposure to radiation and timed according to the standard, the test specimens did not display any visible discolorations.

On the other hand, test specimens employing amines as reducing agents under identical conditions resulted in readily observed discolorations.

EXAMPLES 17-19

A mixture of
9.3 g Bis-GMA,
7.8 g triethyleneglycoldimethacrylate,
6.9 g urethanedimethacrylate, obtained by the reaction of 1 mol of trimethylhexamethylenediisocyanate with 2 moles of 2-hydroxyethylmethacrylate,
23.1 g silicon dioxide, of fine particle size, obtained by high temperature hydrolysis,
2.6 g aluminum oxide, of fine particle size,
50.3 g splinter polymer, obtained by the polymerization of a mixture triethyleneglycoldimethacrylate and silicon dioxide of fine particle size, obtained by high temperature hydrolysis, and powdering in a conventional manner (e.g. German Pat. No. 24 03 211), and
X photoinitiator (see Table 4)
is placed into a small glass tube (6 mm inside diameter and 30 mm high) which is shielded with aluminum foil in such a way that no light can enter through the sides. The mixture is exposed to the radiation of a tungsten lamp (250 W/24 V made by Philips) at a distance of 17 cm for 2 minutes. The portion of the mixture which did not polymerize is removed and the thickness of the layer of the formed body is measured.

Table 4 reports the kind and quantity of the photoinitiator and the thickness of the layer.

TABLE 4

| Example | Initiator | Weight % | Thickness of Layer, mm |
|---|---|---|---|
| 17 | Camphorquinone + | 0.2 | 5.4 |
| | Benzylmeldrum acid = Benzyl malonic acid isopropylidene ester | 0.2 | |
| 18 | Camphorquinone + | 0.2 | 5.2 |
| | Phenylmeldrum acid = Phenyl malonic acid isopropylidene ester | 0.2 | |
| 19 | Camphorquinone + | 0.2 | 5.2 |
| | Ethylmeldrum acid = Ethyl malonic acid isopropylidene ester | 0.2 | |

I claim:

1. In a process for the production of dental compositions by the photopolymerization of at least one vinyl monomer in the presence of a photoinitiator, the improvement comprising polymerizing said at least one vinyl monomer in the presence of a photoinitiator comprising:

(a) at least one photosensitizer of the formula

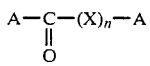

wherein
X is selected from the group consisting of CO, $C(R^1)(R^2)$ and $C(R^3)(OR^4)$, wherein $R^1$, $R^2$, $R^3$, $R^4$ are each selected from the group consisting of hydrogen and a hydrocarbon radical;
n is 0 or 1; and
A is selected from hydrocarbon radicals which may be substituted and which may be bonded together with the proviso that when n is 1 and X is $C(R^1)(R^2)$, and when n is 0, A is an aromatic radical; and (b) at least one reducing agent having the formula

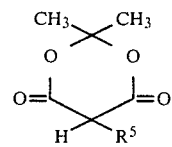

wherein $R^5$ is selected from the group consisting of alkyl, substituted alkyl, aryl, substituted aryl, aralkyl and substituted aralkyl.

2. The process of claim 1 wherein $R^5$ is an alkyl group having 1-5 carbon atoms or a substituted alkyl group wherein the alkyl radical has 1-5 carbon atoms.

3. The process of claim 1 wherein $R^5$ is phenyl.

4. The process of claim 1 wherein $R^5$ is benzyl.

5. The process of claim 1 wherein $R^5$ is substituted alkyl and the substituents are selected from the group consisting of acyl, acyloxy, alkoxysulfonyl and aryloxysulfonyl.

6. The process of claim 1 wherein $R^5$ is substituted aryl and the substituents are selected from the group consisting of alkyl, acyl, acyloxy, alkoxysulfonyl and aryloxysulfonyl.

7. The process of claim 1 wherein $R^5$ is substituted aralkyl and the substituents are selected from the group consisting of alkyl, acyl, acyloxy, alkoxysulfonyl and aryloxysulfonyl.

8. The process of claim 1 wherein the amount of each of the photosensitizer and the reducing agent is $10^{-2}$ to 10% by weight.

9. The process of claim 8 wherein the photosensitizer is camphorquinone.

10. The process of claim 1 wherein the photosensitizer is camphorquinone.

11. The process of claim 1 wherein the reducing agent is selected from the group consisting of benzylmeldrum acid and phenylmeldrum acid.

12. A photopolymerizable dental material comprising at least one vinyl monomer and a photoinitiator comprising:

(a) at least one photosensitizer of the formula

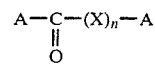

wherein
X is selected from the group consisting of CO, $C(R^1)(R^2)$ and $C(R^3)(OR^4)$, wherein $R^1$, $R^2$, $R^3$, $R^4$ are each selected from the group consisting of hydrogen and a hydrocarbon radical;
n is 0 or 1; and
A is selected from hydrocarbon radicals which may be substituted and which may be bonded together with the proviso that when n is 1 and X is $C(R^1)(R^2)$, and when n is 0, A is an aromatic radical; and (b) at least one reducing agent having the formula

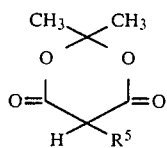

wherein $R^5$ is selected from the group consisting of alkyl, substituted alkyl, aryl, substituted aryl, aralkyl and substituted aralkyl.

13. In a process for the production of dental compositions by the photopolymerization of at least one vinyl monomer in the presence of a photoinitiator, the improvement comprising polymerizing said at least one vinyl monomer in the presence of a photoinitiator comprising:

(a) at least one photosensitizer of the formula

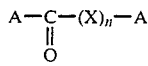

wherein

X is selected from the group consisting of CO, $C(R^1)(R^2)$ and $C(R^3)(OR^4)$; wherein $R^1$, $R^2$, $R^3$, $R^4$ are each selected from the group consisting of hydrogen and a hydrocarbon radical;

n is 0 or 1; and

A is selected from hydrocarbon radicals which may be substituted and which may be bonded together with the proviso that when n is 1 and X is $C(R^1)(R^2)$, and when n is 0, A is an aromatic radical; and (b) a reducing agent having the formula

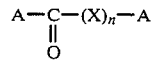

14. The process of claim 13 wherein said photosenitizer is camphorquinone.

15. The process of claim 13 wherein the amount of the photosensitizer is $10^{-2}$ to 10% by weight.

16. The process of claim 13 wherein the amount of the reducing agent is $10^{-2}$ to 10% by weight.

17. The process of claim 13 wherein said photosensitizer is camphorquinone, the amount of each of said photosensitizer and said reducing agent being $10^{-2}$ to 10% by weight.

18. A photopolymerizable dental material comprising at least one vinyl monomer and a photoinitiator comprising (a) at least one photosensitizer of the formula $$A-\underset{\underset{O}{\|}}{C}-(X)_n-A$$

wherein

X is selected from the group consisting of CO, $C(R^1)(R^2)$ and $C(R^3)(OR^4)$; wherein $R^1$, $R^2$, $R^3$, $R^4$ are each selected from the group consisting of hydrogen and a hydrocarbon radical;

n is 0 or 1; and

A is selected from hydrocarbon radicals which may be substituted and which may be bonded together with the proviso that when n is 1 and X is $C(R^1)(R^2)$, and when n is 0, A is an aromatic radical; and (b) a reducing agent having the formula

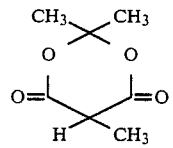

19. The process of claim 9 wherein $R^5$ is ethyl.

* * * * *